United States Patent [19]
Bandman et al.

[11] Patent Number: 6,043,033
[45] Date of Patent: Mar. 28, 2000

[54] HUMAN PROSTATE-ASSOCIATED PROTEASE

[75] Inventors: Olga Bandman, Mountain View; Preeti Lal, Sunnyvale, both of Calif.

[73] Assignee: Incyte Pharmaceuticals, Inc., Palo Alto, Calif.

[21] Appl. No.: 08/807,151

[22] Filed: Feb. 27, 1997

[51] Int. Cl.[7] .............................. C12Q 1/68; C12N 9/50; C12N 9/64; C07H 21/04
[52] U.S. Cl. .............................. 435/6; 435/213; 435/219; 435/226; 435/252.3; 435/254.11; 435/320.1; 435/325; 536/23.2
[58] Field of Search ..................................... 435/219, 213, 435/226, 320.1, 325, 252.3, 254.11, 6; 536/23.2, 24.31

[56] References Cited

PUBLICATIONS

Martin et al. Homo sapiens (subclone H8 6 el from P1 35 H5 C8) DNA sequence, Genbank/Embl Accession No. L35677, Release Date Aug. 22, 1994.

Henttu, P., et. al., "Prostate–specific Antigen and Human Glandular Kallikrein: Two Kallikreins of the Human Prostate" *Annals of Medicine*, 26: 157–164 (1994).

Cramer, S.D., et. al., "Prostate specific antigen cleaves parathyroid hormone–related protein in the PTH–like domain: inactivation of PTHrP–stimulated cAMP Accumulation in Mouse Osteoblasts" *The Journal of Urology*, 156: 526–531 (1996).

Bridon, D.P., et. al., "Structural comparison of prostate–specific antigen and human glandular kallikrein using molecular modeling", *Urology*, 45: 801–806 (1995).

Fukushima, D., et. al., "Nucleotide Sequence of Cloned cDNA for Human Pancreatic Kallikrein", *Biochemistry*, 24: 8037–8043 (1985).

LaVallie, E.R., et. al., "Cloning and Functional Expression of a cDNA Encoding the Catalytic Subunit of Bovine Enterokinase", *The Journal of Biological Chemistry*, 268: 23311–23317 (1993).

LaVallie, E.R., et. al., (GI 416132) GenBank Sequence Database (Accession L19663) National Center for Biotechnology Information: National Library of Medicine, Bethesda, Maryland 2084.

LaVallie, E.R., et. al., (GI 416131) GenBank Sequence Database (Accession L19663) National Center for Biotechnology Information: National Library of Medicine, Bethesda, Maryland 2084.

Fukushima, D., et. al., (GI 186653) GenBank Sequence Database (Accession M25629) National Center for Biotechnology Information: National Library of Medicine, Bethesda, Maryland 2084.

Fukushima, D., et. al., (GI 186652) GenBank Sequence Database (Accession M25629) National Center for Biotechnology Information: National Library of Medicine, Bethesda, Maryland 2084.

Fahnestock M., et. al., (GI 55527) GenBank Sequence Database (Accession X17352) National Center for Biotechnology Information: National Library of Medicine, Bethesda, Maryland 2084.

Fahnestock, M., et. al., (GI 55526) GenBank Sequence Database (Accession X17352) National Center for Biotechnology Information: National Library of Medicine, Bethesda, Maryland 2084.

Fahnestock, M., et. al., "Characterization of kallikrein cDNAs from the African rodent Mastomys" *DNA and Cell Biology*, 13(3): 293–300 (1994).

Christensson, A., et. al., "Enzymatic activity of prostate–specific antigen and its reactions with extracellular serine proteinase inhibitors" *Eur. J. Biochem.*, 194: 755–763 (1990).

Riegman, P.H.J., et. al., "Characterization of the Human Kallikrein Locus", *Genomics*, 14: 6–11 (1992).

*Primary Examiner*—Robert A. Wax
*Attorney, Agent, or Firm*—Lynn E. Murry; Incyte Pharmaceuticals, Inc.

[57] ABSTRACT

The present invention provides a human prostate-associated protease (HUPAP) and polynucleotides which identify and encode HUPAP. The invention also provides expression vectors, host cells, antibodies, antagonists, and antisense molecules. The invention also provides methods for treating disorders associated with expression of HUPAP.

10 Claims, 5 Drawing Sheets

```
                10                  19                  28                  37                  46                  55
5' CAA CTC TNN TAC GAT CAC TAT AGG GAA AGC TGG TAG CCT GCA GGT ACC GGT CCG 64                  73                  82                  91                  100                 109
GAA TTC CCG GGT CGA CCC ACG CGT CCG AGC GGA TCC ACC AGC TTT ATG AAA CTG
                                                                    M   K   L 118                 127                 136                 145                 154                 163
AAC ACA AGT GCC GGC AAT GTC GAT ATC TAT AAA AAA CTG TAC CAC AGT GAT GCC
 N   T   S   A   G   N   V   D   I   Y   K   K   L   Y   H   S   D   A 172                 181                 190                 199                 208                 217
TGT TCT TCA AAA GCA GTG GTT TCT TTA CGC TGT ATA GCC TGC GGG GTC AAC TTG
 C   S   S   K   A   V   V   S   L   R   C   I   A   C   G   V   N   L 226                 235                 244                 253                 262                 271
AAC TCA AGC CGC CAG AGC AGG ATC GTG GGC GGC GAG AGC GCG CTC CCG GGG GCC
 N   S   S   R   Q   S   R   I   V   G   G   E   S   A   L   P   G   A 280                 289                 298                 307                 316                 325
TGG CCC TGG CAG GTC AGC CTG CAC GTC CAG AAC GTC CAC GTG TGC GGA GGC TCC
 W   P   W   Q   V   S   L   H   V   Q   N   V   H   V   C   G   G   S 334                 343                 352                 361                 370                 379
ATC ATC ACC CCC GAG TGG ATC GTG ACA GCC GCC CAC TGC GTG GAA AAA CCT CTT
 I   I   T   P   E   W   I   V   T   A   A   H   C   V   E   K   P   L 388                 397                 406                 415                 424                 433
AAC AAT CCA TGG CAT TGG ACG GCA TTT GCG GGG ATT TTG AGA CAA TCT TTC ATG
 N   N   P   W   H   W   T   A   F   A   G   I   L   R   Q   S   F   M 442                 451                 460                 469                 478                 487
TTC TAT GGA GCC GGA TAC CAA GTA GAA AAA GTG ATT TCT CAT CCA AAT TAT GAC
 F   Y   G   A   G   Y   Q   V   E   K   V   I   S   H   P   N   Y   D 496                 505                 514                 523                 532                 541
TCC AAG ACC AAG AAC AAT GAC ATT GCG CTG ATG AAG CTG CAG AAG CCT CTG ACT
 S   K   T   K   N   N   D   I   A   L   M   K   L   Q   K   P   L   T 550                 559                 568                 577                 586                 595
TTC AAC GAC CTA GTG AAA CCA GTG TGT CTG CCC AAC CCA GGC ATG ATG CTG CAG
 F   N   D   L   V   K   P   V   C   L   P   N   P   G   M   M   L   Q 604                 613                 622                 631                 640                 649
CCA GAA CAG CTC TGC TGG ATT TCC GGG TGG GGG GCC ACC GAG GAG AAA GGG AAG
 P   E   Q   L   C   W   I   S   G   W   G   A   T   E   E   K   G   K
```

FIGURE 1A

```
     658         667         676         685         694         703
ACC TCA GAA GTG CTG AAC GCT GCC AAG GTG CTT CTC ATT GAG ACA CAG AGA TGC
 T   S   E   V   L   N   A   A   K   V   L   L   I   E   T   Q   R   C 712         721         730         739         748         757
AAC AGC AGA TAT GTC TAT GAC AAC CTG ATC ACA CCA GCC ATG ATC TGT GCC GGC
 N   S   R   Y   V   Y   D   N   L   I   T   P   A   M   I   C   A   G 766         775         784         793         802         811
TTC CTG CAG GGG AAC GTC GAT TCT TGC CAG GGT GAC AGT GGA GGG CNT CTG GTC
 F   L   Q   G   N   V   D   S   C   Q   G   D   S   G   G   X   L   V 820         829         838         847         856         865
ACT TCG AAG AAC AAT ATC TGG TGG CTG ATA GGG GAT ACA AGC TGG GGT TCT GGC
 T   S   K   N   N   I   W   W   L   I   G   D   T   S   W   G   S   G 874         883         892         901         910         919
TGT GCC AAA GCT TAC AGA CCA GGA GTG TAC GGG AAT GTG ATG GTA TTC ACG GAC
 C   A   K   A   Y   R   P   G   V   Y   G   N   V   M   V   F   T   D 928         937         946         955         964         973
TGG ATT TAT CGA CAA ATG AGG GCA GAC GGC TAA TCC ACA TGG TCT TCG TCC TTG
 W   I   Y   R   Q   M   R   A   D   G   *   S   T   W   S   S   S   L 982         991        1000        1009        1018        1027
ACG TCG TTT TAC AAG AAA ACA ATG GGG CTG GTT TTG CTT CCC CGT GCA TGA TTT
 T   S   F   Y   K   K   T   M   G   L   V   L   L   P   R   A 1036        1045        1054        1063        1072
ACT CTT AGA GAT GAT TCA GAG GTC ACT TCA TTT TTA TTA AAC AGT GAA CT 3'
```

FIGURE 1B

```
1    M K L N T S A G N V D I Y K K L Y H S D A C S S K A V V S L   SEQ ID NO-1
1    - - - - - - - - - - - - - - - - - - - - - - - - - - - - - -   GI 416132
1    M W F - - - - - - - L V L C L A L S L G - - - - - - - - - -   GI 186653
1    M W F - - - - - - - L I L F L A L F L G - - - - - - - - - -   GI 55527

31   R C I A C G V N L N S S R Q S R I V G G E S A L P G A W P W   SEQ ID NO-1
1    - - - - - - - - - - - - - - I V G G S D S R E G A W P W       GI 416132
14   - - - - - G T G A A P P I Q S R I V G G W E C E Q H S Q P W   GI 186653
14   - - - - - G I D A A P P V Q S R I I G G F N C E K N S Q P W   GI 55527

61   Q V S L H V Q N V H V C G G S I I T P E W I V T A A H C V E   SEQ ID NO-1
15   V V A L Y F D D Q Q V C G A S L V S R D W L V S A A H C V Y   GI 416132
39   Q A A L Y H F S T F Q C G G I L V H R Q W V L T A A H C I S   GI 186653
39   H V A V Y R F A R Y Q C G G V L L D A N W V L T A A H C Y N   GI 55527

91   K P L N N P W H W - - - - - - - - - T A F A G I L R Q S F M   SEQ ID NO-1
45   G R N M E P S K W - - - - - - - - - K A V L G - L H M A S N   GI 416132
69   D N Y Q L - - - W L G R H N L F D D E N T A Q F V H V S E S   GI 186653
69   D K Y Q V - - - W L G K N N R F E D E P S A Q H Q L I S K A   GI 55527

112  F Y G A G Y Q - - - V E K V I S H P N Y D S K T K N N D I A   SEQ ID NO-1
65   L T S P Q I E T R L I D Q I V I N P H Y N K R R K N N D I A   GI 416132
96   F P H P G F N M S L L E - - - N H T R Q A D E D Y S H D L M   GI 186653
96   I P H P G F N M S L L N K - - D H T P H P E D D Y S N D L M   GI 55527

139  L M K L Q K P L - T F N D L V K P V C L P N P G M M L Q P E   SEQ ID NO-1
95   M M H L E M K V - N Y T D Y I Q P I C L P E E N Q V F P P G   GI 416132
123  L L R L T E P A D T I T D A V K V V E L P T Q E P E V - - G   GI 186653
124  L V R L K K P A E - I T D V V K P I D L P T E E P T V - - G   GI 55527

168  Q L C W I S G W G A T E E K G K T - - S E V L N A A K V L L   SEQ ID NO-1
124  R I C S I A G W G A L I Y Q G S T - - A D V L Q E A D V P L   GI 416132
151  S T C L A S G W G S I E P - E N F S F P D D L Q C V D L K I   GI 186653
151  S R C L A S G W G S T T P T E E F E Y S H D L Q C V Y L E L   GI 55527

196  I E T Q R C N S R Y V - Y D N L I T P A M I C A G F L Q G N   SEQ ID NO-1
152  L S N E K C Q Q Q M P E Y N - - I T E N M V C A G Y E A G G   GI 416132
180  L P N D E C E K A H V Q - - - K V T D F M L C V G H L E G G   GI 186653
181  L S N E V C A K A H T E - - - K V T D T M L C A G E M D G G   GI 55527

225  V D S C Q G D S G G X L V T S K N N I W W L I G D T S W G S   SEQ ID NO-1
180  V D S C Q G D S G G P L M C Q E N N R W L L A G V T S F G Y   GI 416132
207  K D T C V G D S G G P L M C D G V - - - - L Q G V T S W G Y   GI 186653
208  K D T C V G D S G G P L I C D G V - - - - L Q G I T S W G P   GI 55527

255  G - C A K A Y R P G V Y G N V M V F T D W I Y R Q M R A D G   SEQ ID NO-1
210  Q - C A L P N R P G V Y A R V P R F T E W I Q S F L H         GI 416132
233  V P C G T P N K P S V A V R V L S Y V K W I E D T I A E N S   GI 186653
234  T P C A L P N V P G I Y T K L I E Y R S W I K D V M A N N P   GI 55527
```

FIGURE 2

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 283 amino acids (B) TYPE: amino acid
(C) STRANDEDNESS: single
(D) TOPOLOGY: linear (vii) IMMEDIATE SOURCE:
(A) LIBRARY: SCORN0T01
(B) CLONE: 556016

(xi) SEQUENCE DESCRIPTION: SEQ ID NO:1:

```
Met Lys Leu Asn Thr Ser Ala Gly Asn Val Asp Ile Tyr Lys Lys Leu
 1               5                  10                  15

Tyr His Ser Asp Ala Cys Ser Ser Lys Ala Val Val Ser Leu Arg Cys
                20                  25                  30

Ile Ala Cys Gly Val Asn Leu Asn Ser Ser Arg Gln Ser Arg Ile Val
                35                  40                  45

Gly Gly Glu Ser Ala Leu Pro Gly Ala Trp Pro Trp Gln Val Ser Leu
 50                  55                  60

His Val Gln Asn Val His Val Cys Gly Gly Ser Ile Ile Thr Pro Glu
 65                  70                  75                  80

Trp Ile Val Thr Ala Ala His Cys Val Glu Lys Pro Leu Asn Asn Pro
                 85                  90                  95

Trp His Trp Thr Ala Phe Ala Gly Ile Leu Arg Gln Ser Phe Met Phe
                100                 105                 110

Tyr Gly Ala Gly Tyr Gln Val Glu Lys Val Ile Ser His Pro Asn Tyr
                115                 120                 125

Asp Ser Lys Thr Lys Asn Asn Asp Ile Ala Leu Met Lys Leu Gln Lys
                130                 135                 140

Pro Leu Thr Phe Asn Asp Leu Val Lys Pro Val Cys Leu Pro Asn Pro
145                 150                 155                 160

Gly Met Met Leu Gln Pro Glu Gln Leu Cys Trp Ile Ser Gly Trp Gly
                165                 170                 175

Ala Thr Glu Glu Lys Gly Lys Thr Ser Glu Val Leu Asn Ala Ala Lys
                180                 185                 190

Val Leu Leu Ile Glu Thr Gln Arg Cys Asn Ser Arg Tyr Val Tyr Asp
                195                 200                 205

Asn Leu Ile Thr Pro Ala Met Ile Cys Ala Gly Phe Leu Gln Gly Asn
                210                 215                 220

Val Asp Ser Cys Gln Gly Asp Ser Gly Gly Xaa Leu Val Thr Ser Lys
225                 230                 235                 240

Asn Asn Ile Trp Trp Leu Ile Gly Asp Thr Ser Trp Gly Ser Gly Cys
                245                 250                 255

Ala Lys Ala Tyr Arg Pro Gly Val Tyr Gly Asn Val Met Val Phe Thr
                260                 265                 270

Asp Trp Ile Tyr Arg Gln Met Arg Ala Asp Gly
                275                 280
```

(2) INFORMATION FOR SEQ ID NO:2:

(i) SEQUENCE CHARACTERISTICS:
(A) LENGTH: 1077 base pairs
(B) TYPE: nucleic acid
(C) STRANDEDNESS: single
(D) TOPOLOGY: linear (vii) IMMEDIATE SOURCE:
(A) LIBRARY: SCORN0T01
(B) CLONE: 556016

(xi) SEQUENCE DESCRIPTION: SEQ ID NO:2:

-continued

```
GCAACTCTNN TACGATCACT ATAGGGAAAG CTGGTAGCCT GCAGGTACCG GTCCGGAATT      60

CCCGGGTCGA CCCACGCGTC CGAGCGGATC CACCAGCTTT ATGAAACTGA ACACAAGTGC     120

CGGCAATGTC GATATCTATA AAAAACTGTA CCACAGTGAT GCCTGTTCTT CAAAAGCAGT     180

GGTTTCTTTA CGCTGTATAG CCTGCGGGGT CAACTTGAAC TCAAGCCGCC AGAGCAGGAT     240

CGTGGGCGGC GAGAGCGCGC TCCCGGGGGC CTGGCCCTGG CAGGTCAGCC TGCACGTCCA     300

GAACGTCCAC GTGTGCGGAG GCTCCATCAT CACCCCCGAG TGGATCGTGA CAGCCGCCCA     360

CTGCGTGGAA AAACCTCTTA CAATCCATG GCATTGACG GCATTTGCGG GGATTTTGAG      420

ACAATCTTTC ATGTTCTATG GAGCCGGATA CCAAGTAGAA AAAGTGATTT CTCATCCAAA     480

TTATGACTCC AAGACCAAGA ACAATGACAT TGCGCTGATG AAGCTGCAGA AGCCTCTGAC     540

TTTCAACGAC CTAGTGAAAC CAGTGTGTCT GCCCAACCCA GGCATGATGC TGCAGCCAGA     600

ACAGCTCTGC TGGATTTCCG GGTGGGGGGC CACCGGAGGA AAAGGGAAGA CCTCAGAAGT     660

GCTGAACGCT GCCAAGGTGC TTCTCATTGA GACACAGAGA TGCAACAGCA GATATGTCTA     720

TGACAACCTG ATCACACCAG CCATGATCTG TGCCGGCTTC CTGCAGGGGA ACGTCGATTC     780

TTGCCAGGGT GACAGTGGAG GGCNTCTGGT CACTTCGAAG AACAATATCT GGTGGCTGAT     840

AGGGGATACA AGCTGGGGTT CTGGCTGTGC CAAAGCTTAC AGACCAGGAG TGTACGGGAA     900

TGTGATGGTA TTCACGGACT GGATTTATCG ACAAATGAGG GCAGACGGCT AATCCACATG     960

GTCTTCGTCC TTGACGTCGT TTTACAAGAA AACAATGGGG CTGGTTTTGC TTCCCCGTGC    1020

ATGATTTACT CTTAGAGATG ATTCAGAGGT CACTTCATTT TTATTAAACA GTGAACT      1077
```

(2) INFORMATION FOR SEQ ID NO:3:

(i) SEQUENCE CHARACTERISTICS:
        (A) LENGTH: 235 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 416132

(xi) SEQUENCE DESCRIPTION: SEQ ID NO:3:

```
Ile Val Gly Gly Ser Asp Ser Arg Glu Gly Ala Trp Pro Trp Val Val
 1               5                  10                  15

Ala Leu Tyr Phe Asp Asp Gln Gln Val Cys Gly Ala Ser Leu Val Ser
            20                  25                  30

Arg Asp Trp Leu Val Ser Ala Ala His Cys Val Tyr Gly Arg Asn Met
        35                  40                  45

Glu Pro Ser Lys Trp Lys Ala Val Leu Gly Leu His Met Ala Ser Asn
    50                  55                  60

Leu Thr Ser Pro Gln Ile Glu Thr Arg Leu Ile Asp Gln Ile Val Ile
65                  70                  75                  80

Asn Pro His Tyr Asn Lys Arg Lys Asn Asn Asp Ile Ala Met Met
                85                  90                  95

His Leu Glu Met Lys Val Asn Tyr Thr Asp Tyr Ile Gln Pro Ile Cys
               100                 105                 110

Leu Pro Glu Glu Asn Gln Val Phe Pro Pro Gly Arg Ile Cys Ser Ile
           115                 120                 125

Ala Gly Trp Gly Ala Leu Ile Tyr Gln Gly Ser Thr Ala Asp Val Leu
       130                 135                 140

Gln Glu Ala Asp Val Pro Leu Leu Ser Asn Glu Lys Cys Gln Gln Gln
```

-continued

```
            145                 150                 155                 160

Met Pro Glu Tyr Asn Ile Thr Glu Asn Met Val Cys Ala Gly Tyr Glu
                    165                 170                 175

Ala Gly Gly Val Asp Ser Cys Gln Gly Asp Ser Gly Gly Pro Leu Met
                180                 185                 190

Cys Gln Glu Asn Asn Arg Trp Leu Leu Ala Gly Val Thr Ser Phe Gly
            195                 200                 205

Tyr Gln Cys Ala Leu Pro Asn Arg Pro Gly Val Tyr Ala Arg Val Pro
        210                 215                 220

Arg Phe Thr Glu Trp Ile Gln Ser Phe Leu His
225                 230                 235

(2) INFORMATION FOR SEQ ID NO:4:

(i) SEQUENCE CHARACTERISTICS:
        (A) LENGTH: 262 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 186653

(xi) SEQUENCE DESCRIPTION: SEQ ID NO:4:

Met Trp Phe Leu Val Leu Cys Leu Ala Leu Ser Leu Gly Gly Thr Gly
1               5                   10                  15

Ala Ala Pro Pro Ile Gln Ser Arg Ile Val Gly Gly Trp Glu Cys Glu
                20                  25                  30

Gln His Ser Gln Pro Trp Gln Ala Ala Leu Tyr His Phe Ser Thr Phe
            35                  40                  45

Gln Cys Gly Gly Ile Leu Val His Arg Gln Trp Val Leu Thr Ala Ala
        50                  55                  60

His Cys Ile Ser Asp Asn Tyr Gln Leu Trp Leu Gly Arg His Asn Leu
65                  70                  75                  80

Phe Asp Asp Glu Asn Thr Ala Gln Phe Val His Val Ser Glu Ser Phe
                85                  90                  95

Pro His Pro Gly Phe Asn Met Ser Leu Leu Glu Asn His Thr Arg Gln
                100                 105                 110

Ala Asp Glu Asp Tyr Ser His Asp Leu Met Leu Leu Arg Leu Thr Glu
            115                 120                 125

Pro Ala Asp Thr Ile Thr Asp Ala Val Lys Val Val Glu Leu Pro Thr
        130                 135                 140

Gln Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                165                 170                 175

Leu Lys Ile Leu Pro Asn Asp Glu Cys Glu Lys Ala His Val Gln Lys
            180                 185                 190

Val Thr Asp Phe Met Leu Cys Val Gly His Leu Glu Gly Gly Lys Asp
        195                 200                 205

Thr Cys Val Gly Asp Ser Gly Gly Pro Leu Met Cys Asp Gly Val Leu
    210                 215                 220

Gln Gly Val Thr Ser Trp Gly Tyr Val Pro Cys Gly Thr Pro Asn Lys
225                 230                 235                 240

Pro Ser Val Ala Val Arg Val Leu Ser Tyr Val Lys Trp Ile Glu Asp
                245                 250                 255
```

```
Thr Ile Ala Glu Asn Ser
                260
```

(2) INFORMATION FOR SEQ ID NO:5:

(i) SEQUENCE CHARACTERISTICS:
        (A) LENGTH: 263 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 55527

(xi) SEQUENCE DESCRIPTION: SEQ ID NO:5:

```
Met Trp Phe Leu Ile Leu Phe Leu Ala Leu Phe Leu Gly Gly Ile Asp
 1               5                  10                  15

Ala Ala Pro Pro Val Gln Ser Arg Ile Ile Gly Gly Phe Asn Cys Glu
                20                  25                  30

Lys Asn Ser Gln Pro Trp His Val Ala Val Tyr Arg Phe Ala Arg Tyr
            35                  40                  45

Gln Cys Gly Gly Val Leu Leu Asp Ala Asn Trp Val Leu Thr Ala Ala
        50                  55                  60

His Cys Tyr Asn Asp Lys Tyr Gln Val Trp Leu Gly Lys Asn Asn Arg
65                  70                  75                  80

Phe Glu Asp Glu Pro Ser Ala Gln His Gln Leu Ile Ser Lys Ala Ile
                85                  90                  95

Pro His Pro Gly Phe Asn Met Ser Leu Leu Asn Lys Asp His Thr Pro
            100                 105                 110

His Pro Glu Asp Asp Tyr Ser Asn Asp Leu Met Leu Val Arg Leu Lys
        115                 120                 125

Lys Pro Ala Glu Ile Thr Asp Val Val Lys Pro Ile Asp Leu Pro Thr
    130                 135                 140

Glu Glu Pro Thr Val Gly Ser Arg Cys Leu Ala Ser Gly Trp Gly Ser
145                 150                 155                 160

Thr Thr Pro Thr Glu Glu Phe Glu Tyr Ser His Asp Leu Gln Cys Val
                165                 170                 175

Tyr Leu Glu Leu Leu Ser Asn Glu Val Cys Ala Lys Ala His Thr Glu
            180                 185                 190

Lys Val Thr Asp Thr Met Leu Cys Ala Gly Glu Met Asp Gly Gly Lys
        195                 200                 205

Asp Thr Cys Val Gly Asp Ser Gly Gly Pro Leu Ile Cys Asp Gly Val
    210                 215                 220

Leu Gln Gly Ile Thr Ser Trp Gly Pro Thr Pro Cys Ala Leu Pro Asn
225                 230                 235                 240

Val Pro Gly Ile Tyr Thr Lys Leu Ile Glu Tyr Arg Ser Trp Ile Lys
                245                 250                 255

Asp Val Met Ala Asn Asn Pro
                260
```

HUMAN PROSTATE-ASSOCIATED PROTEASE

FIELD OF THE INVENTION

This invention relates to nucleic acid and amino acid sequences of a novel human prostate-associated protease and to the use of these sequences in the diagnosis, prevention, and treatment of gastrointestinal disorders, cancer, and prostate disorders.

BACKGROUND OF THE INVENTION

Prostate-specific antigen (PSA) is a 33 kD glycoprotein synthesized in the epithelial cells of the prostate gland. It is a secreted serine protease of the kallikrein family. PSA has been shown to digest the seminal vesicle protein, semenogelin, parathyroid hormone-related protein, and insulin-like growth factor-binding protein-3 (Henttu P. et al. (1994) Ann. Med. 26: 157–164; Cramer S. D. et al. (1996) J. Urol. 156: 526–531).

Genes encoding the three human kallikreins, tissue kallikrein (KLK1), glandular kallikrein (KLK2), and PSA, are located in a cluster at chromosome map position 19q13.2–q13.4 (Riegmen P. H. (1992) Genomics 14: 6–11). PSA shares more extensive homology with KLK2 than with KLK1. Both PSA and KLK2 are produced by prostate epithelial cells, and their expression is regulated by androgens. Three amino acid residues were found to be critical for serine protease activity, residues $H_{65}$, $D_{120}$, and $S_{213}$ in PSA (Bridon D. P. et al. (1995) Urology 45: 801–806). Substrate specificity, described as chymotrypsinogen-like (with KLK2) or trypsin-like (with PSA), is thought to be determined by $S_{207}$ in PSA and $D_{209}$ in KLK2 (Bridon et al., supra). KLK1 is chymotrypsinogen-like and expressed in the pancreas, urinary system, and sublingual gland. KLK1, like the other kallikreins, is made as a pre-pro-protein and is processed into an active form of 238 amino acids by cleavage of a 24 amino acid terminal signal sequence (Fukushima D. et al. (1985) Biochemistry 24: 8037–8043).

Adenocarcinoma of the prostate accounts for a significant number of malignancies in men over 50, and over 122,000 new cases occur per year in the United States alone. Prostate-specific antigen (PSA) is the most sensitive marker available for monitoring cancer progression and response to therapy. Serum PSA is elevated in up to 92% of patients with prostatic carcinoma, and serum concentration depends upon tumor volume. Since PSA is also moderately elevated in patients with benign prostate hyperplasia, additional techniques are needed to distinguish between the two.

The enterokinases (also called enteropeptidases) are a functionally distinct family of serine proteases with homology to PSA and the kallikreins. Enterokinases act in a multi-step enzymatic cascade that allows the digestion of exogenous macromolecules without destroying similar endogenous material. This cascade results in the conversion of pancreatic proenzymes to active enzymes in the lumen of the gut. Trypsin, chymotrypsin, and carboxypeptidase A are examples of pancreatic enzymes activated by intestinal enterokinases. Enterokinase has a high specificity for the amino acid sequence $(Asp)_4$-Lys, a motif found in the amino-termini of trypsinogens from a wide range of species. Congenital deficiency in enterokinase may cause life-threatening intestinal malabsorption.

The catalytic subunit of bovine enterokinase was cloned and characterized by LaVallie E. R. et al. (1993, J. Biol. Chem. 268: 23311–23317). The bovine enterokinase is a serine protease with four predicted intramolecular disulfide bonds and shares homology with other serine proteases, such as the kallikreins and hepsin. Like the kallikreins, bovine enterokinase has characteristic active site histidine, aspartic acid, and serine residues at conserved positions.

Discovery of proteins related to PSA, enterokinase, and the polynucleotides encoding them satisfies a need in the art by providing new compositions useful in diagnosis, prevention, and treatment of gastrointestinal disorders, cancer, and prostate disorders.

SUMMARY OF THE INVENTION

The present invention features a novel human prostate-associated kallikrein, hereinafter designated HUPAP, and characterized as having chemical and structural similarity to serine proteases such as bovine enterokinase, human pancreatic kallikrein, and rat renal kallikrein.

Accordingly, the invention features a substantially purified HUPAP which has the amino acid sequence shown in SEQ ID NO:1.

One aspect of the invention features isolated and substantially purified polynucleotides that encode HUPAP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under highly stringent wash conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HUPAP. The present invention also features antibodies which bind specifically to HUPAP, and pharmaceutical compositions comprising substantially purified HUPAP. The invention also features the use of agonists and antagonists of HUPAP. The invention also features a method for producing HUPAP using the host cell, and methods for treating cancer and prostatic hyperplasia by administering an antagonist to HUPAP. The invention also features methods for treating gastrointestinal disorders by administering HUPAP or an agonist to HUPAP. In addition, the invention features methods for treating cancer and prostate disorders by administering an antagonist to HUPAP.

BRIEF DESCRIPTION OF THE FIGURES

FIGS. 1A and 1B show the amino acid sequence (SEQ ID NO:1) and nucleic acid sequence (SEQ ID NO:2) of HUPAP. The alignment was produced using MACDNASIS PRO software (Hitachi Software Engineering Co., Ltd., San Bruno, Calif.).

FIG. 2 shows the amino acid sequence alignments among HUPAP (SEQ ID NO:1), bovine enterokinase (GI 416132; SEQ ID NO:3), human pancreatic kallikrein (GI 186653; SEQ ID NO:4), and African rat renal kallikrein (GI 55527; SEQ ID NO:5). The alignment was produced using the multisequence alignment program of LASERGENE software (DNASTAR Inc, Madison, Wis.).

DESCRIPTION OF THE INVENTION

Figure 3:
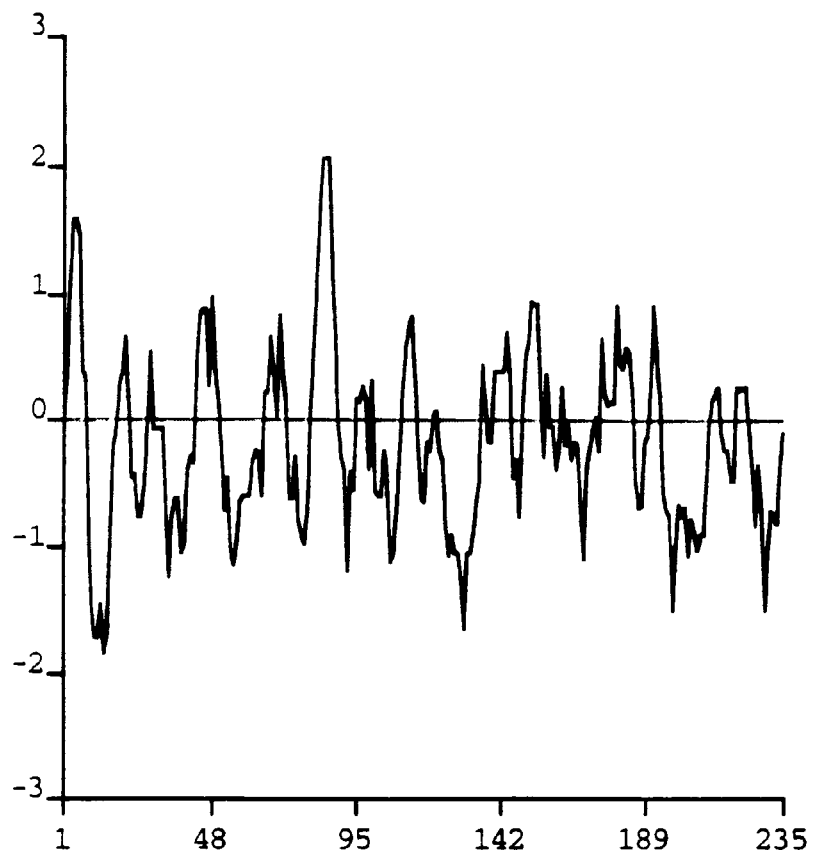
FIG. 3 shows the hydrophobicity plot (MACDNASIS PRO software) for HUPAP, SEQ ID NO:1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence", as used herein, refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HUPAP, as used herein, refers to the amino acid sequences of substantially purified HUPAP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using the XL-PCR kit (Perkin Elmer, Norwalk, Conn.) in the 5' and/or the 3' direction and resequenced, or which has been assembled from the overlapping sequences of more than one Incyte clone using the GELVIEW Fragment Assembly system (GCG, Madison, Wis.), or which has been both extended and assembled.

A "variant" of HUPAP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HUPAP, or any oligopeptide thereof, to induce a specific immune response in appropriate animals or cells and to bind with specific antibodies.

The term "agonist", as used herein, refers to a molecule which, when bound to HUPAP, causes a change in HUPAP which modulates the activity of HUPAP. Agonists may include proteins, nucleic acids, carbohydrates, or any other molecules which bind to HUPAP.

The terms "antagonist" or "inhibitor", as used herein, refer to a molecule which, when bound to HUPAP, blocks or modulates the biological or immunological activity of HUPAP. Antagonists and inhibitors may include proteins, nucleic acids, carbohydrates, or any other molecules which bind to HUPAP.

The term "modulate", as used herein, refers to a change or an alteration in the biological activity of HUPAP. Modulation may be an increase or a decrease in protein activity, a change in binding characteristics, or any other change in the biological, functional or immunological properties of HUPAP.

The term "mimetic", as used herein, refers to a molecule, the structure of which is developed from knowledge of the structure of HUPAP or portions thereof and, as such, is able to effect some or all of the actions of protease-like molecules.

The term "derivative", as used herein, refers to the chemical modification of a nucleic acid encoding HUPAP or the encoded HUPAP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete, when total complementarity exists between the single stranded molecules. The degree of complementarity between nucleic acid strands has significant effects on the efficiency and strength of hybridization between nucleic acid strands. This is of particular importance in amplification reactions which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered; and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HUPAP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HUPAP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HUPAP in a sample and thereby correlates with expression of the transcript from the polynucleotide encoding the protein.

"Alterations" in the polynucleotide of SEQ ID NO:2, as used herein, comprise any alteration in the sequence of polynucleotides encoding HUPAP including deletions, insertions, and point mutations that may be detected using hybridization assays. Included within this definition is the detection of alterations to the genomic DNA sequence which encodes HUPAP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding HUPAP (e.g., using fluorescent in situ hybridization [FISH] to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind HUPAP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human protease, (HUPAP), the polynucleotides encoding HUPAP, and the use of these compositions for the diagnosis, prevention, or treatment of gastrointestinal disorders, cancer, and prostate disorders.

Nucleic acids encoding the human HUPAP of the present invention were first identified in Incyte Clone 556016 from the spinal cord tissue cDNA library (SCORNOT01) through a computer-generated search for amino acid sequence alignments. A consensus sequence, SEQ ID NO:2, was derived from the following overlapping and/or extended nucleic acid sequences: Incyte Clones 556016 (SCORNOT01), 842889 (PROSTUT05), and 991163 (COLNNOT11).

Figure 4:
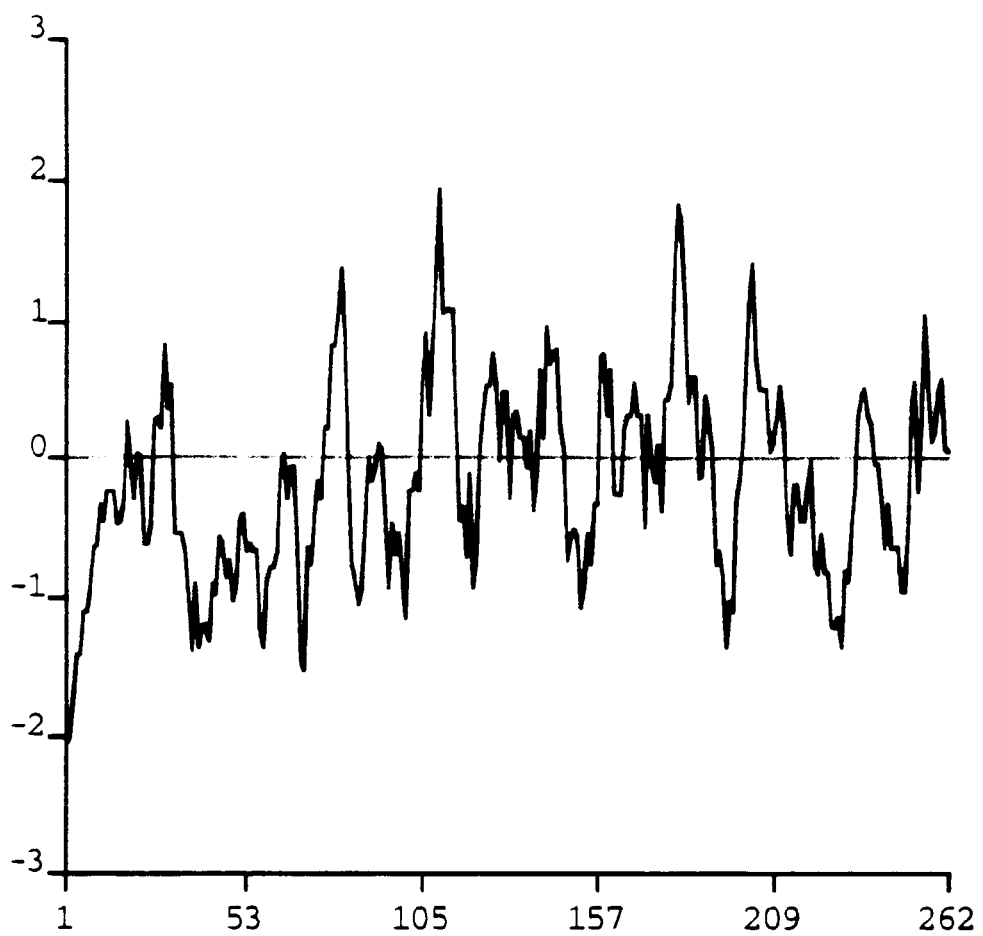
FIG. 4 shows the hydrophobicity plot for human pancreatic kallikrein, SEQ ID NO:4.

In one embodiment, the invention encompasses a polypeptide comprising the amino acid sequence of SEQ ID NO:1, as shown in FIGS. 1A and 1B. HUPAP is 283 amino acids in length and has a potential N-glycosylation sites at asparagine residue 4. HUPAP has chemical and structural homology with bovine enterokinase (GI 416132; SEQ ID NO:3), human pancreatic kallikrein (GI 186653; SEQ ID NO:4), and African rat renal kallikrein (GI 55527; SEQ ID NO:5). In particular, HUPAP and bovine enterokinase share 38% identity. The amino acid sequence from $C_{22}$ to $S_{45}$ near HUPAP's amino terminus is hydrophilic and resembles sequences important for membrane attachment or secretion (FIGS. 2, 3, and 4). HUPAP sequence contains conserved residues critical for serine protease activity, $H_{87}$, $D_{138}$, and $S_{232}$ (FIG. 2). Amino acid residue $D_{226}$ is likely to confer on HUPAP chymotrypsinogen-like activity. HUPAP amino acid sequence includes 8 conserved cysteine residues (72, 88, 156, 170, 201, 217, 228, and 256; FIG. 2). In the serine proteases mentioned above, these cysteines are structurally important and form four disulfide bonds. As illustrated by FIGS. 3 and 4, HUPAP and human pancreatic kallikrein have rather similar hydrophobicity plots. Northern analysis reveals expression of this sequence in the prostate gland, colon, and pancreas. Of seven tissue samples in which HUPAP is expressed, four are from prostate glands, and three of these are from cancer patients.

The invention also encompasses HUPAP variants. A preferred HUPAP variant is one having at least 80%, and more preferably 90%, amino acid sequence similarity to the HUPAP amino acid sequence (SEQ ID NO:1). A most preferred HUPAP variant is one having at least 95% amino acid sequence similarity to SEQ ID NO:1.

The invention also encompasses polynucleotides which encode HUPAP. Accordingly, any nucleic acid sequence which encodes the amino acid sequence of HUPAP can be used to generate recombinant molecules which express HUPAP. In a particular embodiment, the invention encompasses the polynucleotide comprising the nucleic acid sequence of SEQ ID NO:2 as shown in FIGS. 1A and 1B.

It will be appreciated by those skilled in the art that as a result of the degeneracy of the genetic code, a multitude of nucleotide sequences encoding HUPAP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HUPAP, and all such variations are to be considered as being specifically disclosed.

Although nucleotide sequences which encode HUPAP and its variants are preferably capable of hybridizing to the nucleotide sequence of the naturally occurring HUPAP under appropriately selected conditions of stringency, it may be advantageous to produce nucleotide sequences encoding HUPAP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUPAP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode HUPAP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding HUPAP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding HUPAP which are encompassed by the invention include deletions, insertions, or substitutions of different nucleotides resulting in a polynucleotide that encodes the same or a functionally equivalent HUPAP. The encoded protein may also contain deletions, insertions, or substitutions of amino acid residues which produce a silent change and result in a functionally equivalent HUPAP. Deliberate amino acid substitutions may be made on the basis of similarity in polarity, charge, solubility, hydrophobicity, hydrophilicity, and/or the amphipathic nature of the residues as long as the biological activity of HUPAP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding HUPAP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase DNA Polymerase (USB, Cleveland, Ohio), Taq polymerase (Perkin Elmer), thermostable T7 polymerase (Amersham Pharmacia Biotech Piscataway, N.J.), or combinations of recombinant polymerases and proofreading exonucleases such as the ELONGASE amplification system (Life Technologies, Gaithersburg, Md.). Preferably, the process is automated with machines such as the Microlab 2200 (Hamilton, Reno, Nev.), DNA Engine thermal cycler (PTC200; MJ Research, Watertown, Mass.) and the ABI 377 DNA sequencers (Perkin Elmer).

The nucleic acid sequences encoding HUPAP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HUPAP, or fusion proteins or functional equivalents thereof, may be used in recombinant DNA molecules to direct expression of HUPAP in appropriate host cells. Due to the inherent degeneracy of the genetic code, other DNA sequences which encode substantially the same or a functionally equivalent amino acid sequence may be produced and these sequences may be used to clone and express HUPAP.

As will be understood by those of skill in the art, it may be advantageous to produce HUPAP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter HUPAP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding HUPAP may be ligated to a heterologous sequence to encode a fusion protein. For example, to screen peptide libraries for inhibitors of HUPAP activity, it may be useful to encode a chimeric HUPAP protein that can be recognized by a commercially available antibody. A fusion protein may also be engineered to contain a cleavage site located between the HUPAP encoding sequence and the heterologous protein sequence, so that HUPAP may be cleaved and purified away from the heterologous moiety.

In another embodiment, sequences encoding HUPAP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 7:225–232). Alternatively, the protein itself may be produced using chemical methods to synthesize the amino acid sequence of HUPAP, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of HUPAP, or any part thereof, may be altered during direct synthesis and/or combined using chemical methods with sequences from other proteins, or any part thereof, to produce a variant polypeptide.

In order to express a biologically active HUPAP, the nucleotide sequences encoding HUPAP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HUPAP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding HUPAP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Life Technologies) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HUPAP, vectors based on SV40 or EBV may be used with an appropriate selectable marker.

In bacterial systems, a number of expression vectors may be selected depending upon the use intended for HUPAP. For example, when large quantities of HUPAP are needed for the induction of antibodies, vectors which direct high level expression of fusion proteins that are readily purified may be used. Such vectors include, but are not limited to, the multifunctional *E. coli* cloning and expression vectors such as the BLUESCRIPT phagemid (Stratagene), in which the sequence encoding HUPAP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (*1987*) Methods Enzymol. 153:516–544.

In cases where plant expression vectors are used, the expression of sequences encoding HUPAP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HUPAP. For example, in one such system, *Autographa californica* nuclear polyhedrosis virus (AcNPV) is used as a vector to express foreign genes in *Spodoptera frugiperda* cells or in Trichoplusia larvae. The sequences encoding HUPAP may be cloned into a non-essential region of the virus, such as the polyhedrin gene, and placed under control of the polyhedrin promoter. Successful insertion of HUPAP will render the polyhedrin gene inactive and produce recombinant virus lacking coat protein. The recombinant viruses may then be used to infect, for example, *S. frugiperda* cells or Trichoplusia larvae in which HUPAP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HUPAP may be ligated into an adenovirus transcription/translation complex consisting of the late promoter and tripartite leader sequence. Insertion in a non-essential E1 or E3 region of the viral genome may be used to obtain a viable virus which is capable of expressing HUPAP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding HUPAP. Such signals include the ATG initiation codon and adjacent sequences. In cases where sequences encoding HUPAP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HUPAP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HUPAP is inserted within a marker gene sequence, recombinant cells containing sequences encoding HUPAP can be identified by the absence of marker gene function. Alternatively, a marker gene can be placed in tandem with a sequence encoding HUPAP under the control of a single promoter. Expression of the marker gene in response to induction or selection usually indicates expression of the tandem gene as well.

Alternatively, host cells which contain the nucleic acid sequence encoding HUPAP and express HUPAP may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding HUPAP can be detected by DNA—DNA or DNA-RNA hybridization or amplification using probes or portions or fragments of polynucleotides encoding HUPAP. Nucleic acid amplification based assays involve the use of oligonucleotides or oligomers based on the sequences encoding HUPAP to detect transformants containing DNA or RNA encoding HUPAP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HUPAP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HUPAP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HUPAP include oligolabeling, nick translation, end-labeling or PCR amplification using a labeled nucleotide. Alternatively, the sequences encoding HUPAP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Amersham Pharmacia Biotech, Promega, and USB). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding HUPAP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HUPAP may be designed to contain signal sequences which direct secretion of HUPAP through a prokaryotic or eukaryotic cell membrane. Other recombinant constructions may be used to join sequences encoding HUPAP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and HUPAP may be used to facilitate purification. One such expression vector provides for expression of a fusion protein containing HUPAP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying HUPAP from the fusion protein. A discussion of vectors which contain fusion proteins is provided in Kroll, D. J. et al. (1993; DNA Cell Biol. 12:441–453).

In addition to recombinant production, fragments of HUPAP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of HUPAP may be chemically synthesized separately and combined using chemical methods to produce the full length molecule.

Therapeutics

HUPAP, a serine protease which appears to function in the prostate gland, shares chemical and structural homology with bovine enterokinase, human pancreatic kallikrein, and African rat renal kallikrein. In addition, northern analysis shows that four cDNA libraries containing HUPAP transcripts are from prostate tissue and three of these libraries were from patients with prostate cancer. HUPAP expression was also found in spinal cord, colon tissue, and pancreatic islet cells. Thus, HUPAP expression appears to be most closely associated with both the prostate gland and the gastrointestinal system.

HUPAP's protease activity may activate certain digestive enzymes. Therefore, in one embodiment, HUPAP or a fragment or derivative thereof may be administered to a subject to treat or prevent a gastrointestinal disorder including, but not limited to, congenital enterokinase deficiency, pancreatitis, and ulcerative colitis.

In another embodiment, a vector capable of expressing HUPAP, or a fragment or a derivative thereof, may also be administered to a subject to treat or prevent gastrointestinal disorders including, but not limited to, the gastrointestinal disorders listed above.

In another embodiment, agonists which are specific for HUPAP may be used to stimulate or prolong the activity of HUPAP and may be administered to a subject to treat or prevent gastrointestinal disorders including, but not limited to, the gastrointestinal disorders listed above.

Antagonists or inhibitors of HUPAP may be used to suppress excessive cell proliferation. Thus in one embodiment, antagonists or inhibitors of HUPAP may be administered to a subject to treat or prevent cancer including, but not limited to, adenocarcinomas, sarcomas, and cancer of the prostate, pancreas, small intestine, large intestine, stomach, esophagus, and colon.

More specifically, antagonists or inhibitors of HUPAP may be used to suppress excessive proliferation of prostate cells. Thus in another embodiment, antagonists or inhibitors of HUPAP may be administered to a subject to treat or prevent prostate disorders including, but not limited to, benign prostatic hyperplasia or cancer.

In other aspects, antibodies which are specific for HUPAP may be used directly as an antagonist, or indirectly as a targeting or delivery mechanism for bringing a pharmaceutical agent to cells or tissue which express HUPAP.

In another embodiment, a vector expressing antisense of the polynucleotide encoding HUPAP may be administered to a subject to treat or prevent cancer including, but not limited to, the cancers listed above.

In another embodiment, a vector expressing antisense of the polynucleotide encoding HUPAP may be administered to a subject to treat or prevent prostate disorders including, but are not limited to, benign prostatic hyperplasia.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of HUPAP may be produced using methods which are generally known in the art. In particular, purified HUPAP may be used to produce antibodies or to screen libraries of pharmaceutical agents to identify those which specifically bind HUPAP.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HUPAP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HUPAP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HUPAP amino acids may be fused with those of another protein such as keyhole limpet hemocyanin and antibody produced against the chimeric molecule.

Monoclonal antibodies to HUPAP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HUPAP-specific single chain antibodies. Antibodies with related specificity, but of distinct idiotypic composition, may be generated by chain shuffling from random combinatorial immunoglobulm libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HUPAP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HUPAP and its specific antibody. A two-site, monoclonal-based immunoassay utilizing monoclonal antibodies reactive to two non-interfering HUPAP epitopes is preferred, but a competitive binding assay may also be employed (Maddox, supra).

In another embodiment of the invention, the polynucleotides encoding HUPAP, or any fragment thereof, or antisense molecules, may be used for therapeutic purposes. In one aspect, antisense to the polynucleotide encoding HUPAP may be used in situations in which it would be desirable to block the transcription of the mRNA. In particular, cells may be transformed with sequences complementary to polynucleotides encoding HUPAP. Thus, antisense molecules may be used to modulate HUPAP activity, or to achieve regulation of gene function. Such technology is now well known in the art, and sense or antisense oligomers or larger fragments, can be designed from various locations along the coding or control regions of sequences encoding HUPAP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding HUPAP. These techniques are described both in Sambrook et al. (supra) and in Ausubel et al. (supra).

Genes encoding HUPAP can be turned off by transforming a cell or tissue with expression vectors which express high levels of a polynucleotide or fragment thereof which encodes HUPAP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HUPAP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HUPAP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUPAP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HUPAP, antibodies to HUPAP, mimetics, agonists, antagonists, or inhibitors of HUPAP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HUPAP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HUPAP or fragments thereof, antibodies of HUPAP, agonists, antagonists or inhibitors of HUPAP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HUPAP may be used for the diagnosis of conditions or diseases characterized by expression of HUPAP, or in assays to monitor patients being treated with HUPAP, agonists, antagonists or inhibitors. The antibodies useful for diagnostic purposes may be prepared in the same manner as those described above for therapeutics. Diagnostic assays for HUPAP include methods which utilize the antibody and a label to detect HUPAP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HUPAP are known in the art and provide a basis for diagnosing altered or abnormal levels of HUPAP expression. Normal or standard values for HUPAP expression are established by combining body fluids or cell extracts taken from normal mammalian subjects, preferably human, with antibody to HUPAP under conditions suitable for complex formation. The amount of standard complex formation may be quantified by various methods, but preferably by photometric means. Quantities of HUPAP expressed in subject, control, and disease, samples from biopsied tissues are compared with the standard values. Deviation between standard and subject values establishes the parameters for diagnosing disease.

In another embodiment of the invention, the polynucleotides encoding HUPAP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HUPAP may be correlated with disease. The diagnostic assay may be used to distinguish between absence, presence, and excess expression of HUPAP, and to monitor regulation of HUPAP levels during therapeutic intervention.

In one aspect, hybridization with PCR probes which are capable of detecting polynucleotide sequences, including genomic sequences, encoding HUPAP or closely related molecules, may be used to identify nucleic acid sequences which encode HUPAP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HUPAP, alleles, or related sequences.

Probes may also be used for the detection of related sequences, and should preferably contain at least 50% of the nucleotides from any of the HUPAP encoding sequences. The hybridization probes of the subject invention may be DNA or RNA and derived from the nucleotide sequence of SEQ ID NO:2 or from genomic sequence including promoter, enhancer elements, and introns of the naturally occurring HUPAP.

Means for producing specific hybridization probes for DNAs encoding HUPAP include the cloning of nucleic acid sequences encoding HUPAP or HUPAP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HUPAP may be used for the diagnosis of conditions or diseases which are associated with expression of HUPAP. Examples of such conditions or diseases include ulcerative colitis, prostatic hyperplasia, and cancers of the prostate and colon. The polynucleotide sequences encoding HUPAP may be used in Southern or northern analysis, dot blot, or other membrane-based technologies; in PCR technologies; or in dip stick, pIN, ELISA or chip assays utilizing fluids or tissues from patient biopsies to detect altered HUPAP expression. Such qualitative or quantitative methods are well known in the art.

In a particular aspect, the nucleotide sequences encoding HUPAP may be useful in assays that detect activation or induction of various cancers, particularly those mentioned above. The nucleotide sequences encoding HUPAP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HUPAP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HUPAP, a normal or standard profile for expression is established. This may be accomplished by combining body fluids or cell extracts taken from normal subjects, either animal or human, with a sequence, or a fragment thereof, which encodes HUPAP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUPAP may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HUPAP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode HUPAP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HUPAP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HUPAP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HUPAP and the agent being tested, may be measured.

Another technique for drug screening which may be used provides for high throughput screening of compounds having suitable binding affinity to the protein of interest as described in published PCT application WO84/03564. In this method, as applied to HUPAP large numbers of different small test compounds are synthesized on a solid substrate, such as plastic pins or some other surface. The test compounds are reacted with HUPAP, or fragments thereof, and washed. Bound HUPAP is then detected by methods well known in the art. Purified HUPAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUPAP specifically compete with a test compound for binding HUPAP. In this manner, the antibodies can be used to detect the presence of any peptide which shares one or more antigenic determinants with HUPAP.

In additional embodiments, the nucleotide sequences which encode HUPAP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I SCORNOT01 cDNA Library Construction

The cDNA library was constructed from normal spinal cord removed from a 71 year old, Caucasian male (lot #RA95-04-0255) obtained from the Keystone Skin Bank, International Institute for Advanced Medicine, Exton, Pa.). The tissue was flash frozen, ground in a mortar and pestle, and lysed immediately in a buffer containing guanidinium isothiocyanate. The lysate was extracted once with acid phenol, pH 4.0, once with phenol chloroform, pH 8.0, and then centrifuged over a CsCl cushion using an Beckman SW28 rotor in a L8-70M ultracentrifuge (Beckman Instruments). The RNA was precipitated from 0.3 M sodium acetate using 2.5 volumes of ethanol, resuspended in water, and treated with DNase for 15 min at 37° C. The poly A+ RNA was isolated with the OLIGOTEX kit (QIAGEN Inc, Chatsworth, Calif.) and used to construct the cDNA library.

The RNA was handled according to the recommended protocols in the SUPERSCRIPT plasmid system (catalog #18248-013; Life Technologies. cDNAs were fractionated on a SEPHAROSE CL4B column (catalog #275105, Amersham Pharmacia Biotech), and those cDNAs exceeding 400 bp were ligated into PSPORT2 plasmid. The plasmid was subsequently transformed into DH5a competent cells (Cat. #18258-012, Life Technologies).

II Isolation and Sequencing of cDNA Clones

Plasmid DNA was purified using the MINIPREP Kit (Catalogue #77468, Advanced Genetic Technologies Corporation, Gaithersburg, Md.), a 96-well block kit with reagents for 960 purifications. The recommended protocol included with the kit was employed except for the following changes. Each of the 96 wells was filled with only 1 ml of sterile Terrific Broth (Catalog #22711, Life Technologies) with carbenicillin at 25 mg/L and glycerol at 0.4%. After the wells were inoculated, the bacteria were cultured for 24 hours and lysed with 60 µl of lysis buffer. A centrifugation step, using a (Beckman GS-6R @2900 rpm for 5 min (Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were prepared and sequenced by the method of Sanger F. and A. R. Coulson (1975; J Mol Biol 94:441f), using MICROLAB 2200 (Hamilton, Reno Nev.) in combination with four DNA Engine thermal cyclers (PTC200; MJ Research) and Applied Biosystems 377 or 373 DNA sequencing systems (Perkin Elmer), and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul S. F. (1993) J. Mol. Evol. 36:290–300; Altschul, S. F. et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and Smith T. F. (1992 Protein Engineering 5:35–51), incorporated herein by reference, can be used when dealing with primary sequence patterns and secondary structure gap penalties. As disclosed in this application, the sequences in the Sequence Listing have a minimum length of at lease 49 nucleotides, and no more than 12% uncalled bases (where N is recorded rather than A, C, G, or T).

The BLAST approach, as detailed in Karlin and Altschul (1993; Proc. Natl. Acad. Sci. 90:5873–7) and incorporated herein by reference, searches matches between a query sequence and a database sequence, to evaluate the statistical significance of any matches found, and to report only those matches which satisfy the user-selected threshold of significance. In this application, threshold was set at 10–25 for nucleotides and 10–14 for peptides.

Incyte nucleotide sequence were searched against the GenBank databases for pri=primate, rod=rodent, and mam=mammalian sequences, and deduced amino acid sequences from the same clones are searched against GenBank functional protein databases, mamp=mammalian, vrtp=vertebrate and eukp=eukaryote, for homology. The relevant database for a particular match were reported as a GIxxx+/−p (where xxx is for pri, rod, etc and p, if found, refers to protein database). The product score=(% nucleotide or amino acid identity [between the query and reference sequences] in Blast multiplied by the % maximum possible BLAST score [based on the lengths of query and reference sequences]) divided by 100. Where an Incyte Clone was homologous to several sequences, up to five matches were provided with their relevant scores. In an analogy to the hybridization procedures used in the laboratory, a conservative, electronic stringency was set at 70 ("exact" match), and the absolute cutoff for was set at 40 (1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HUPAP occurs. Abundance and percent abundance are also reported. Abundance directly reflects the number of times a particular transcript is represented in a cDNA library, and percent abundance is abundance divided by the total number of sequences examined in the cDNA library.

V Extension of HUPAP-Encoding Polynucleotides to Full Length or to Recover Regulatory Sequences Full length HUPAP-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the DNA Engine thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as the QIAQUICK kit (QIAGEN). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 µl of liquid LB/2× Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |

-continued

| | |
|---|---|
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 µCi of [$\gamma$-$^{32}$P] adenosine triphosphate (Amersham Pharmacia Biotech) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots in a PHOSPHOIMAGER cassette (Amersham Pharmacia Biotech) for several hours, hybridization patterns are compared.

VII Antisense Molecules

Antisense molecules to the HUPAP-encoding sequence, or any part thereof, is used to inhibit in vivo or in vitro expression of naturally occurring HUPAP. Although use of antisense oligonucleotides, comprising about 20 base-pairs, is specifically described, essentially the same procedure is used with larger cDNA fragments. An oligonucleotide based on the coding sequences of HUPAP, as shown in FIGS. 1A and 1B, is used to inhibit expression of naturally occurring HUPAP. The complementary oligonucleotide is designed from the most unique 5' sequence as shown in FIGS. 1A and 1B and used either to inhibit transcription by preventing promoter binding to the upstream nontranslated sequence or translation of an HUPAP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A and 1B.

VIII Expression of HUPAP

Expression of HUPAP is accomplished by subcloning the cDNAs into appropriate vectors and transforming the vectors into host cells. In this case, the cloning vector, pSport, previously used for the generation of the cDNA library is used to express HUPAP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HUPAP into the bacterial growth media which can be used directly in the following assay for activity.

IX Demonstration of HUPAP Activity

HUPAP's proteolytic activity can be determined by methods described by Christernsson A. et al. (1990, Eur. J. Biochem. 194: 755–763). Substrates for proteolytic cleavage are found in human semen. Human seminal plasma is collected and coagulated semen is washed free of soluble components. HUPAP is incubated with coagulated semen in a buffer consisting of 50 mmol/l TRIS-HCl pH 7.8, with 0.1 mol/l NaCl. Reactions are performed at 37° C. After incubation periods of different durations (from 0 to 30 minutes) the samples are analyzed by SDS/PAGE. The resulting pattern of peptide fragments is quantitated and compared to a control sample handled identically but to which HUPAP is not added.

X Production of HUPAP Specific Antibodies

HUPAP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using LASERGENE software (LASERGENE Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HUPAP Using Specific Antibodies

Naturally occurring or recombinant HUPAP is substantially purified by immunoaffinity chromatography using antibodies specific for HUPAP. An immunoaffinity column is constructed by covalently coupling HUPAP antibody to an activated chromatographic resin, such as CnBr-activated SEPHAROSE (Amersham Pharmacia Biotech). After the coupling, the resin is blocked and washed according to the manufacturer's instructions.

Media containing HUPAP is passed over the immunoaffinity column, and the column is washed under conditions that allow the preferential absorbance of HUPAP (e.g., high ionic strength buffers in the presence of detergent). The column is eluted under conditions that disrupt antibody/HUPAP binding (eg, a buffer of pH 2–3 or a high concentration of a chaotrope, such as urea or thiocyanate ion), and HUPAP is collected.

XII Identification of Molecules Which Interact with HUPAP

HUPAP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HUPAP, washed and any wells with labeled HUPAP complex are assayed. Data obtained using different concentrations of HUPAP are used to calculate values for the number, affinity, and association of HUPAP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide encoding the human prostate-associated protease of SEQ ID NO:1.

2. A polynucleotide which hybridizes under highly stringent wash conditions of 0.1× saline sodium citrate and 0.5% sodium dodecyl sulfate to the polynucleotide of claim 1.

3. A hybridization probe comprising the polynucleotide of claim 1.

4. An isolated and purified polynucleotide comprising SEQ ID NO:2.

5. A polynucleotide which is complementary to the polynucleotide of claim 1.

6. A hybridization probe comprising the polynucleotide of claim 5.

7. An expression vector containing the polynucleotide of claim 1.

8. A host cell containing the vector of claim 7.

9. A method for producing a polypeptide comprising the amino acid sequence of SEQ ID NO:1, the method comprising the steps of:
   a) culturing the host cell of claim 8 under conditions suitable for the expression of the polypeptide; and
   b) recovering the polypeptide from the host cell culture.

10. A method for detection of a polynucleotide encoding a human prostate-associated protease in a biological sample comprising the steps of:
    a) hybridizing the polynucleotide of claim 5 to nucleic acid material of a biological sample, thereby forming a hybridization complex; and
    b) detecting said hybridization complex, wherein the presence of said complex correlates with the presence of a polynucleotide encoding human prostate-associated protease in said biological sample.

* * * * *